United States Patent
Bari et al.

(10) Patent No.: US 11,970,456 B1
(45) Date of Patent: Apr. 30, 2024

(54) SYNTHESIS OF THIOSEMICARBAZIDE ANALOGUE AS INHIBITOR OF TYROSINASE, SKIN HYPERPIGMENTATION, AND FRUIT AND/OR VEGETABLE BROWNING

(71) Applicant: KING SAUD UNIVERSITY, Riyadh (SA)

(72) Inventors: Ahmed Muhammad Bari, Riyadh (SA); Usman Ghani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/371,092

(22) Filed: Sep. 21, 2023

(51) Int. Cl.
| | |
|---|---|
| C07D 231/56 | (2006.01) |
| A23B 7/154 | (2006.01) |
| A23L 3/3544 | (2006.01) |
| A61K 8/49 | (2006.01) |
| A61Q 19/02 | (2006.01) |

(52) U.S. Cl.
CPC ............ *C07D 231/56* (2013.01); *A23B 7/154* (2013.01); *A23L 3/3544* (2013.01); *A61K 8/494* (2013.01); *A61Q 19/02* (2013.01); *C07B 2200/13* (2013.01)

(58) Field of Classification Search
None
See application file for complete search history.

(56) References Cited

U.S. PATENT DOCUMENTS

2010/0063115 A1   3/2010   Klein et al.

OTHER PUBLICATIONS

Yi et al., European Journal of Medicinal Chemistry (2011), 46(9), pp. 4330-4335.*
Deng et al., Huaxue Shiji (2020), 42(3), pp. 321-325.*

* cited by examiner

*Primary Examiner* — Brian J Davis
(74) *Attorney, Agent, or Firm* — Nath, Goldberg & Meyer; Richard C. Litman (57) ABSTRACT

A 2-((1H-indazol-5-yl)methylene)hydrazinecarbothioamide compound, its synthesis, and its use as a tyrosine kinase inhibitor. In particular, the synthesis of the 2-((1H-indazol-5-yl)methylene)hydrazinecarbothioamide compound as shown below. This compound has a high efficacy of inhibiting mushroom tyrosinase enzyme, and is a potent inhibitor of tyrosinase that can be used as an inhibitor of skin hyperpigmentation as well as an inhibitor of fruit and vegetable browning.

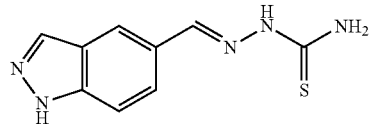

Formula 2

20 Claims, 5 Drawing Sheets

SYNTHESIS OF THIOSEMICARBAZIDE ANALOGUE AS INHIBITOR OF TYROSINASE, SKIN HYPERPIGMENTATION, AND FRUIT AND/OR VEGETABLE BROWNING

BACKGROUND

1. Field

The present disclosure relates to the compound 2-((1H-indazol-5-yl)methylene)hydrazinecarbothioamide, its synthesis, and its use as a potent inhibitor of tyrosinase that can be used as an inhibitor of skin hyperpigmentation as well as an inhibitor of fruit and vegetable browning.

2. Description of the Related Art

Thiosemicarbazone belongs to an important class of sulfur-containing heterocycles that are widely distributed among many drugs available in the market.

Tyrosinase is a copper-containing enzyme that catalyzes the monophenolase activity (hydroxylation of monophenols) and the o-diphenolase activity (oxidation of o-diphenols to o-quinones). Moreover, the ability of thiosemicarbazide to selectively bind to the active site dicopper center of tyrosinase leading to competitive inhibition of the enzyme has been previously documented. The enzyme is commonly distributed in humans, animals, plants, and microorganisms. It is a rate-limiting enzyme in the biosynthesis of melanin pigment in the human skin, hair, and eyes. In dermatology, inhibition of tyrosinase is a pivotal clinical target for treatment of various skin disorders that include but are not limited to post-inflammatory hyperpigmentation, nevus, melanoma, melasma, lentigo, melanoderma, ephelis, and flecks.

*Agaricus bisporus* (mushroom) tyrosinase (EC 1.14.18.1) is a well-studied enzyme, the active site of which is significantly identical to that of other tyrosinase enzymes, besides its easy availability. Moreover, kojic acid is a standard inhibitor of tyrosinase that has been used in various topical preparations for treatment of skin disorders associated with excessive melanogenesis. Various cosmetic products such as lotions and creams contain kojic acid as an active ingredient for its skin-lightening effects.

Tyrosinase inhibition is not only a clinical target for skin disorders but is also an important commercial target for preventing unnecessary fruit and vegetable browning that shortens their shelf life and nutritional value, leading to significant economic losses. In most fruits and vegetables, tyrosinase is expressed in high amounts following bruising, cutting, or damage to the tissue during handling and transportation. Inhibition of tyrosinase is highly desirable for controlling or delaying undesired browning process in fruits and vegetables to prevent economic losses to the industry.

Thus, new molecules having desired activities and solving the aforementioned problems are desired.

SUMMARY

The present subject matter relates to the preparation of new semicarbazone analogues derived from the condensation of thiosemicarbazide with indazole-5-carboxaldehyde. The current subject matter also presents the synthetic capability and the exploitation of the proposed analogue for the inhibition of tyrosinase enzyme. Accordingly, the presently described compound can be effective for treatment of various skin disorders that include but are not limited to post-inflammatory hyperpigmentation, nevus, melanoma, melasma, lentigo, melanoderma, ephelis, and flecks, as well as being useful for preventing unnecessary fruit and vegetable browning.

In an embodiment, the present subject matter relates to a 2-((1H-indazol-5-yl)methylene)hydrazinecarbothioamide compound having the formula 2:

Formula 2 or a hydrochloride, acetate, phosphate, or p-toluene sulfate salt thereof.

In another embodiment, the present subject matter relates to a pharmaceutically acceptable composition comprising a therapeutically effective amount of the 2-((1H-indazol-5-yl)methylene)hydrazinecarbothioamide compound and a dermatologically acceptable carrier.

In a further embodiment, the present subject matter relates to a method of inhibiting tyrosine kinase in a patient comprising administering to a patient in need thereof a therapeutically effective amount of the 2-((1H-indazol-5-yl)methylene)hydrazinecarbothioamide compound.

In an additional embodiment, the present subject matter relates to a method of lightening skin in a patient comprising administering to a patient in need thereof a therapeutically effective amount of the 2-((1H-indazol-5-yl)methylene)hydrazinecarbothioamide compound.

In one more embodiment, the present subject matter relates to a method of preventing bacterial growth in a patient comprising administering to a patient in need thereof a therapeutically effective amount of the 2-((1H-indazol-5-yl)methylene)hydrazinecarbothioamide compound.

In an embodiment, the present subject matter relates to a method of inhibiting tyrosine kinase in a fruit or vegetable comprising administering to a fruit or vegetable a tyrosine kinase inhibiting effective amount of the 2-((1H-indazol-5-yl)methylene)hydrazinecarbothioamide compound.

In another embodiment, the present subject matter relates to a method of preventing bacterial growth in a fruit or vegetable comprising administering to a fruit or vegetable a therapeutically effective amount of the 2-((1H-indazol-5-yl)methylene)hydrazinecarbothioamide compound.

In a further embodiment, the present subject matter relates to a method of making the 2-((1H-indazol-5-yl)methylene)hydrazinecarbothioamide compound, the method comprising: slowly adding, to a solution of indazole-5-carboxaldehyde in ethanol, thiosemicarbazide followed by the addition of acetic acid at room temperature to obtain a reaction mixture; refluxing the reaction mixture with stirring followed by evaporating of solvent to obtain a solid; and washing and recrystallizing the solid with ethanol to obtain the 2-((1H-indazol-5-yl)methylene)hydrazinecarbothioamide compound.

In an additional embodiment, the present subject matter relates to a method of making the 2-((1H-indazol-5-yl)methylene)hydrazinecarbothioamide compound, the method comprising: condensing a thiosemicarbazide with a solution of indazole-5-carboxaldehyde in using acetic acid as a catalyst; and obtaining the 2-((1H-indazol-5-yl)methylene)hydrazinecarbothioamide compound.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a microbial infection.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the preparation of new semicarbazone analogues derived from the condensation of thiosemicarbazide with indazole-5-carboxaldehyde. The current subject matter also presents the synthetic capability and the exploitation of the proposed analogue for the inhibition of tyrosinase enzyme. Accordingly, the presently described compound can be effective for treatment of various skin disorders that include but are not limited to post-inflammatory hyperpigmentation, nevus, melanoma, melasma, lentigo, melanoderma, ephelis, and flecks, as well as being useful for preventing unnecessary fruit and vegetable browning.

In an embodiment, the present subject matter relates to a 2-((1H-indazol-5-yl)methylene)hydrazinecarbothioamide compound having the formula 2:

Formula 2 or a hydrochloride, acetate, phosphate, or p-toluene sulfate salt thereof.

In certain embodiments, the 2-((1H-indazol-5-yl)methylene)hydrazinecarbothioamide compound can be obtained as crystals. In further embodiments, the 2-((1H-indazol-5-yl)methylene)hydrazinecarbothioamide compound can have a melting point of about 258° C. to about 262° C.

In another embodiment, the present subject matter relates to a pharmaceutically acceptable composition comprising a therapeutically effective amount of the 2-((1H-indazol-5-yl)methylene)hydrazinecarbothioamide compound and a dermatologically acceptable carrier.

In an embodiment, the pharmaceutically acceptable composition can be a topical composition. In certain embodiments, the topical composition can be an aerosol, foam, cream, gel, solution, suspension, lotion, cream, ointment, or the like. In another embodiment, the topical composition can be a cream or an ointment.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically, pharmaceutically, or dermatologically effective dosage, e.g., a dosage sufficient to provide treatment for a disease, disorder, or condition as described herein, such as a skin disease, disorder, or condition. Administration of the compound or pharmaceutical compositions thereof can be by any method that delivers the compound topically to an area of interest and/or need.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of a disease, disorder, or condition, any dermatologically acceptable mode of administration can be used with other pharmaceutically acceptable excipients, including solid, semi-solid, liquid or aerosol dosage forms, such as, for example, powders, liquids, suspensions, aerosols or the like.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

In a further embodiment, the present subject matter relates to a method of inhibiting tyrosine kinase in a patient comprising administering to a patient in need thereof a therapeutically effective amount of the 2-((1H-indazol-5-yl)methylene)hydrazinecarbothioamide compound.

In an embodiment, the inhibition of the tyrosine kinase can enable the administration of the 2-((1H-indazol-5-yl)methylene)hydrazinecarbothioamide compound to the patient to treat a skin disorder in the patient selected from the group consisting of post-inflammatory hyperpigmentation, nevus, melanoma, melasma, lentigo, melanoderma, ephelis, flecks, and a combination thereof.

In an additional embodiment, the present subject matter relates to a method of lightening skin in a patient comprising administering to a patient in need thereof a therapeutic ally effective amount of the 2-((1H-indazol-5-yl)methylene)hydrazinecarbothioamide compound.

In one more embodiment, the present subject matter relates to a method of preventing bacterial growth in a patient comprising administering to a patient in need thereof a therapeutically effective amount of the 2-((1H-indazol-5-yl)methylene)hydrazinecarbothioamide compound.

In an embodiment, the present subject matter relates to a method of inhibiting tyrosine kinase in a fruit or vegetable comprising administering to a fruit or vegetable a tyro sine kinase inhibiting effective amount of the 2-((1H-indazol-5-yl)methylene)hydrazinecarbothioamide compound.

In another embodiment, the present subject matter relates to a method of preventing bacterial growth in a fruit or vegetable comprising administering to a fruit or vegetable a therapeutically effective amount of the 2-((1H-indazol-5-yl)methylene)hydrazinecarbothioamide compound.

In an embodiment, the inhibition of the tyrosine kinase enables the administration of the 2-((1H-indazol-5-yl)methylene)hydrazinecarbothioamide compound to prevent browning of the fruit or vegetable.

In a further embodiment, the present subject matter relates to a method of making the 2((1H-indazol-5-yl)methylene)hydrazinecarbothioamide compound, the method comprising: slowly adding, to a solution of indazole-5-carboxaldehyde in ethanol, thiosemicarbazide followed by the addition of acetic acid at room temperature to obtain a reaction mixture; refluxing the reaction mixture with stirring followed by evaporating of solvent to obtain a solid; and washing and recrystallizing the solid with ethanol to obtain the 2-((1H-indazol-5-yl)methylene)hydrazinecarbothioamide compound.

The present production methods can be further seen by referring to the following Scheme 1:

In an embodiment of the present production methods, the refluxing can occur for at least about 3 hours.

In another embodiment of the present production methods, the evaporating of the solvent can occur in vacuo.

In a further embodiment of the present production methods, washing can occur with cold water several times.

In an embodiment of the present production methods, the indazole-5-carboxaldehyde and thiosemicarbazide can be added in an about 1:1.1 molar ratio.

In an additional embodiment of the present production methods, the 2-((1H-indazol-5-yl)methylene)hydrazinecarbothioamide compound can be obtained in an about 85% yield.

In an additional embodiment, the present subject matter relates to a method of making the 2-((1H-indazol-5-yl)methylene)hydrazinecarbothioamide compound, the method comprising: condensing a thiosemicarbazide with a solution of indazole-5-carboxaldehyde in using acetic acid as a catalyst; and obtaining the 2-((1H-indazol-5-yl)methylene)hydrazinecarbothioamide compound.

The following examples relate to various methods of manufacturing the specific compound and application of the same, as described herein. All compound numbers expressed herein are with reference to the synthetic pathway figures shown above.

EXAMPLES

Example 1

Preparation of 2-((1H-indazol-5-yl)methylene)hydrazinecarbothioamide (2)

To a solution of indazole-5-carboxaldehyde 1 (1 mmol) in ethanol (50 mL), thiosemicarbazide (1.1 mmol) was added slowly followed by the addition of 0.05 mL of acetic acid at room temperature. The resulting mixture was refluxed for 3 h with stirring followed by the evaporation of solvent in vacuo. The solid obtained was washed with cold water several times and recrystallized with ethanol, yielded compound 2.

Yield: 85%, M.P. 258-262° C., $^1$HNMR (700.174 MHz, DMSO-$d_6$): δ=7.54 (d, 1H, Ph), 8.01 (q, 3H, NH, Ph), 8.14 (t, 3H, CH, Ph), 11.37 (s, 1H, NH), 13.23 (br s, 1H, NH). $^{13}$C NMR (176.07 MHz, DMSO-$d_6$): δ=111, 122.1, 123.3, 124.7, 127.4, 134.8, 140.9, 143.7, 178.1.

Example 2

Tyrosinase Inhibition Assay and Kinetics

The assay mixture contained sodium phosphate buffer (50 mM; pH 6.8), 22 U of mushroom tyrosinase (EC 1.14.18.1; Sigma Chemical Co., St. Louis, USA), L-DOPA substrate (1 mM), and Compound 2 dissolved in DMSO. The final concentration of DMSO in the assay mixture was 0.5%. The o-diphenolase inhibitory activity of Compound 2 was first screened at a final concentration of 30 μM using Ultrospec 2100 pro spectrophotometer (Amersham Biosciences, UK). The production of dopachrome was measured at 475 nm at 25° C. using kojic acid as a positive control.

The kinetic assays included a range of substrate (0.25-2.0 mM) and Compound 2 concentrations (0.25, 0.5, 1.0, 2.0 μM). The enzyme was first incubated with the enzyme for 15 min. at 25° C. followed by addition of substrate. The reaction was continuously monitored in the spectrophotometer and the enzyme velocity was measured from the linear portion of the curve (7). The kinetics data were analyzed by Grafit 7.0.3 software (Erithacus Software Ltd., Staines, UK) utilizing the Lineweaver Burk plot {1/v versus 1/[S]} and the $K_i$ values were calculated using the Dixon plot {1/v versus [I]}.

Results:

Compound 2 is a new, potent, and selective inhibitor of o-diphenolase activity of mushroom tyrosinase. It is a competitive inhibitor of the enzyme that binds to the active site with a dissociation constant ($K_i$) of 0.0843 μM (IC$_{50}$=0.228 μM) (Table 1).

TABLE 1

| The $K_i$ and IC$_{50}$ values of Compound 2 compared to kojic acid as positive | | | |
|---|---|---|---|
| Inhibitor | $K_i$ (μM ± SEM) | IC$_{50}$ (μM ± SEM) | Type of inhibition |
| Compound 2 | 0.0843 ± 0.0031 | 0.228 ± 0.0075 | Competitive |
| Kojic acid (standard inhibitor) | 4.43 ± 0.20 | 9.1 ± 0.33 | Competitive | control. The $K_i$, value shows that the compound is 52-fold more potent than kojic acid.

Figure 1:
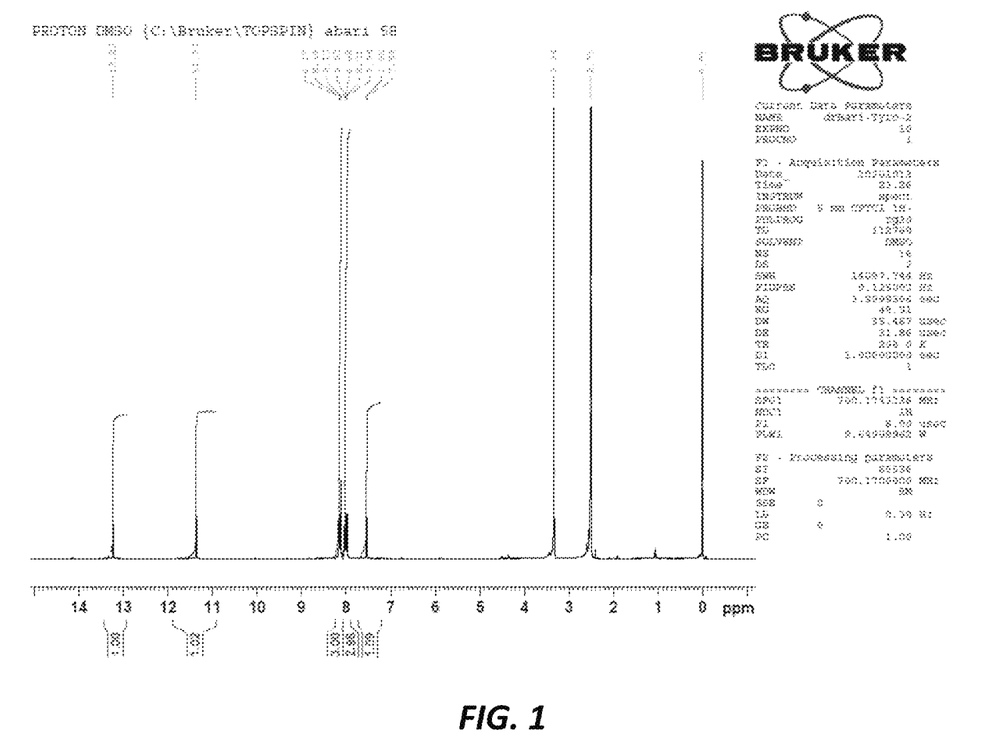
FIG. 1 shows a first $^1$H NMR analysis of the 2-((1H-indazol-5-yl)methylene)hydrazinecarbothioamide compound.
Figure 2:
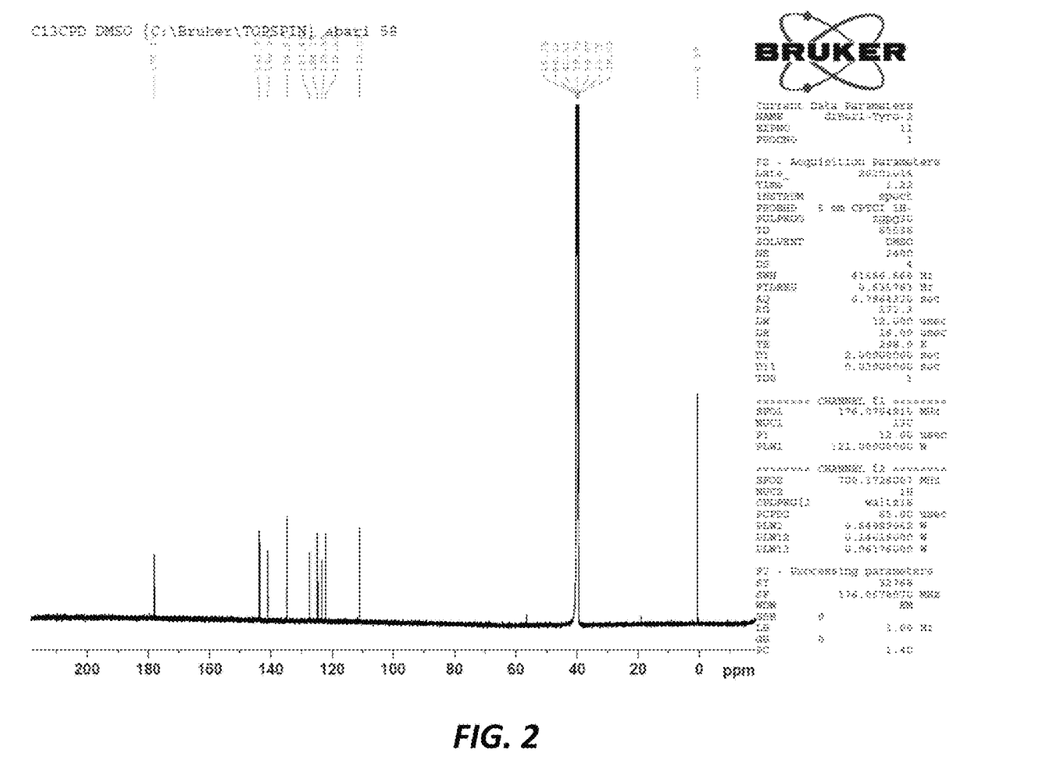
FIG. 2 shows a first $^{13}$C NMR analysis of the 2-((1H-indazol-5-yl)methylene)hydrazinecarbothioamide compound.
Figure 3:
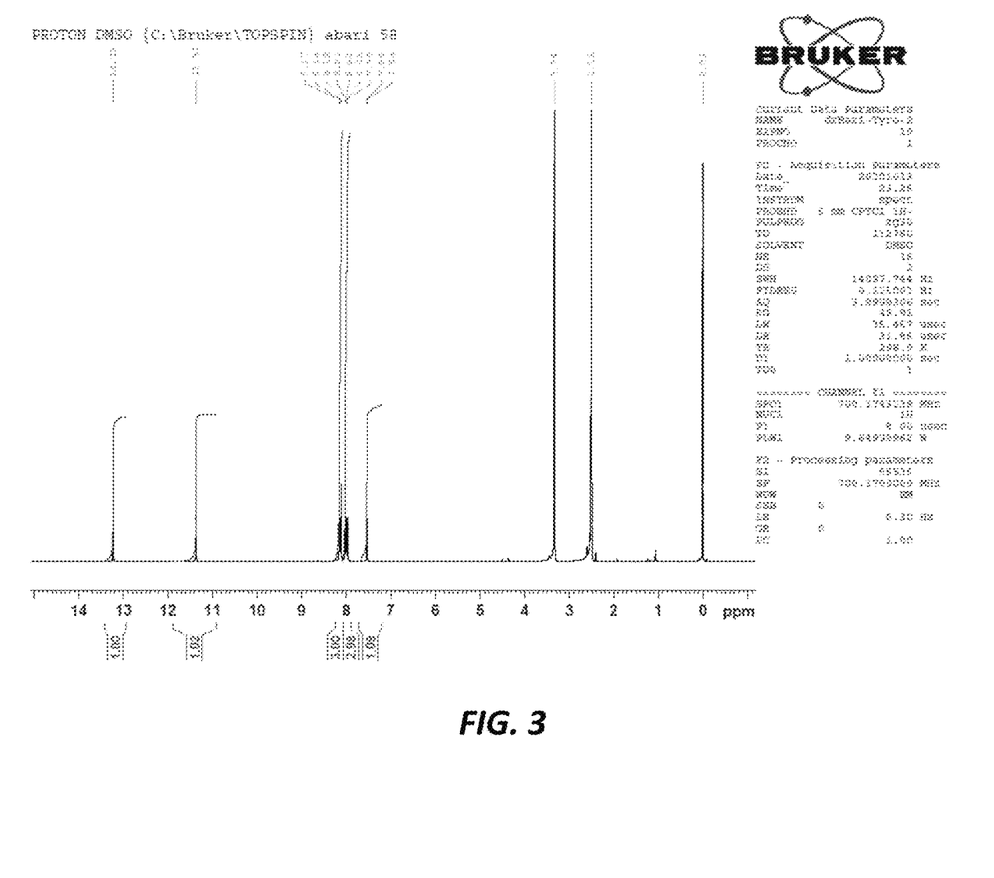
FIG. 3 shows a second $^1$H NMR analysis of the 2-((1H-indazol-5-yl)methylene)hydrazinecarbothioamide compound.
Figure 4:
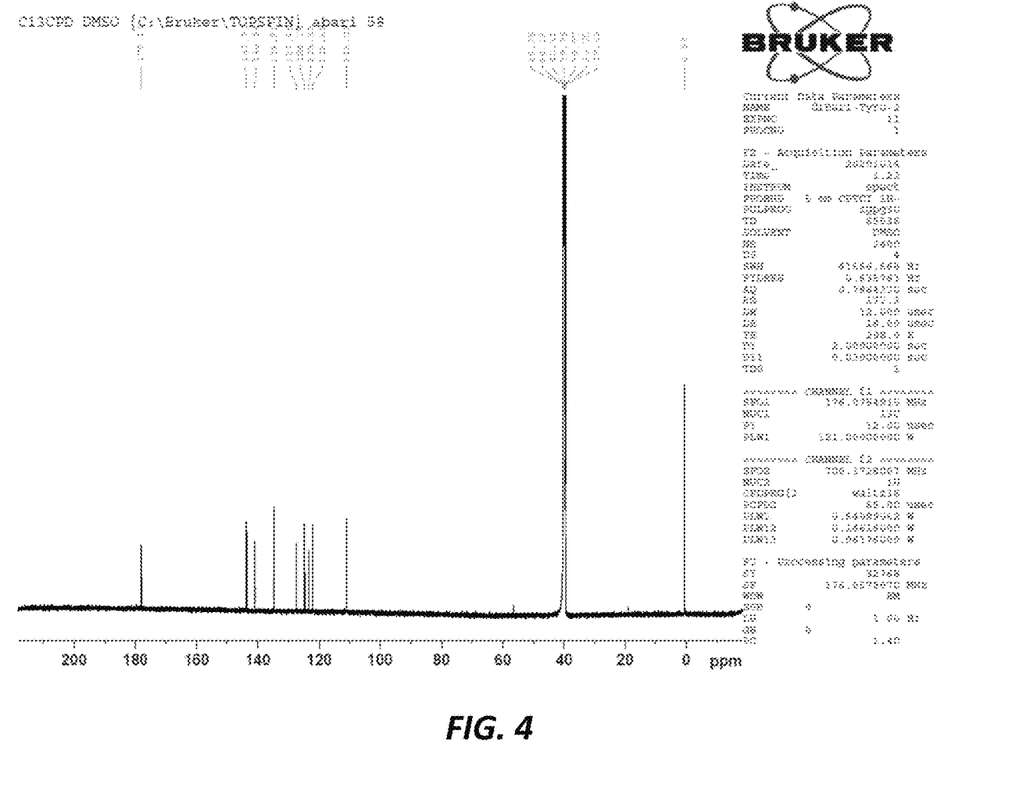
FIG. 4 shows second a $^{13}$C NMR analysis of the 2-((1H-indazol-5-yl)methylene)hydrazinecarbothioamide compound.
Figure 5A:
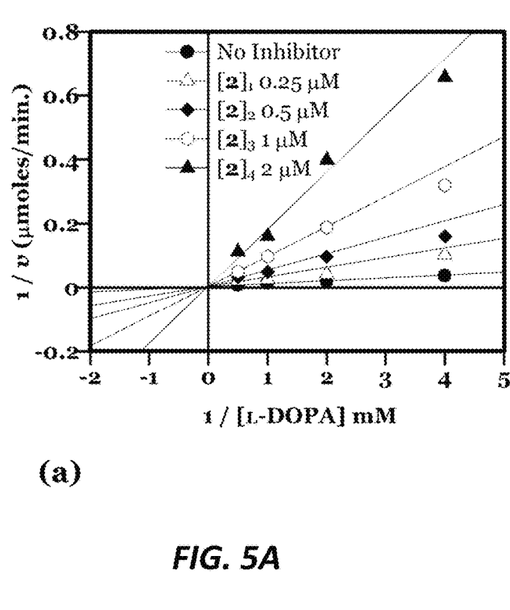
FIGS. 5A-5B are Lineweaver-Burk (5A) and Dixon plots (5B) confirming the competitive inhibition of mushroom tyrosinase by the 2-((1H-indazol-5-yl)methylene)hydrazinecarbothioamide compound.
Figure 5B:
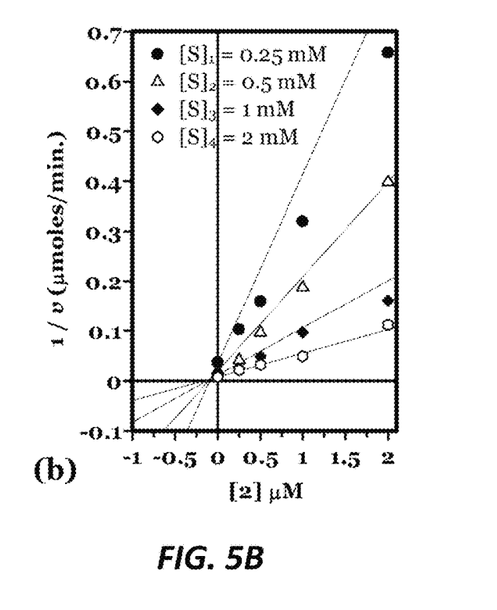

The compound is 52-fold more potent than kojic acid, which is a standard inhibitor of tyrosinase. The Lineweaver Burk and Dixon plots confirm competitive inhibition of tyrosinase by the compound (FIGS. 5A-5B).

Based on its potent inhibitory activity against mushroom tyrosinase, compound 2 can be used as an active ingredient in the methods described herein.

It is to be understood that the 2-((1H-indazol-5-yl)methylene)hydrazinecarbothioamide compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A 2-((1H-indazol-5-yl)methylene)hydrazinecarbothioamide compound having the formula 2:

Formula 2 or a hydrochloride, acetate, phosphate, or p-toluene sulfate salt thereof.

2. The 2-((1H-indazol-5-yl)methylene)hydrazinecarbothioamide compound of claim 1, wherein the compound is obtained as crystals.

3. The 2-((1H-indazol-5-yl)methylene)hydrazinecarbothioamide compound of claim 1, having a melting point of about 258° C. to about 262° C.

4. A pharmaceutically acceptable composition for treating skin disorders comprising a therapeutically effective amount of the 2-((1H-indazol-5-yl)methylene)hydrazinecarbothioamide compound of claim 1 and a dermatologically acceptable carrier.

5. The pharmaceutically acceptable composition of claim 4, wherein the pharmaceutically acceptable composition is a topical composition.

6. The pharmaceutically acceptable composition of claim 5, wherein the topical composition is a cream or an ointment.

7. A method of inhibiting tyrosine kinase in a patient comprising administering to a patient in need thereof a therapeutically effective amount of the 2-((1H-indazol-5-yl)methylene)hydrazinecarbothioamide compound of claim 1.

8. The method of inhibiting tyrosine kinase of claim 7, wherein the inhibition of the tyrosine kinase from the administration of the 2-((1H-indazol-5-yl)methylene)hydrazinecarbothioamide compound to the patient treats a skin disorder in the patient selected from the group consisting of post-inflammatory hyperpigmentation, nevus, melanoma, melasma, lentigo, melanoderma, ephelis, flecks, and a combination thereof.

9. A method of lightening skin in a patient comprising administering to a patient in need thereof a therapeutically effective amount of the 2-((1H-indazol-5-yl)methylene)hydrazinecarbothioamide compound of claim 1.

10. A method of preventing bacterial growth in a patient comprising administering to a patient in need thereof a therapeutically effective amount of the 2-((1H-indazol-5-yl)methylene)hydrazinecarbothioamide compound of claim 1.

11. A method of inhibiting tyrosine kinase in a fruit or vegetable comprising administering to a fruit or vegetable a tyrosine kinase inhibiting effective amount of the 2-((1H-indazol-5-yl)methylene)hydrazinecarbothioamide compound of claim 1.

12. The method of inhibiting tyrosine kinase in a fruit or vegetable of claim 11, wherein the inhibition of the tyrosine kinase from the administration of the 2-((1H-indazol-5-yl)methylene)hydrazinecarbothioamide compound prevents browning of the fruit or vegetable.

13. A method of preventing bacterial growth in a fruit or vegetable comprising administering to a fruit or vegetable a therapeutically effective amount of the 2-((1H-indazol-5-yl)methylene)hydrazinecarbothioamide compound of claim 1.

14. A method of making the 2-((1H-indazol-5-yl)methylene)hydrazinecarbothioamide compound of claim 1, the method comprising:
    adding, to a solution of indazole-5-carboxaldehyde in ethanol, thiosemicarbazide followed by the addition of acetic acid at room temperature to obtain a reaction mixture;
    refluxing the reaction mixture with stirring followed by evaporating of solvent to obtain a solid; and
    washing and recrystallizing the solid with ethanol to obtain the 2-((1H-indazol-5-yl)methylene)hydrazinecarbothioamide compound.

15. The method of making the 2-((1H-indazol-5-yl)methylene)hydrazinecarbothioamide compound of claim 14, wherein the refluxing occurs for at least about 3 hours.

16. The method of making the 2-((1H-indazol-5-yl)methylene)hydrazinecarbothioamide compound of claim 14, wherein the evaporating of the solvent occurs in vacuo.

17. The method of making the 2-((1H-indazol-5-yl)methylene)hydrazinecarbothioamide compound of claim 14, wherein washing occurs with cold water several times.

18. The method of making the 2-((1H-indazol-5-yl)methylene)hydrazinecarbothioamide compound of claim 14, wherein the indazole-5-carboxaldehyde and thiosemicarbazide are added in an about 1:1.1 molar ratio.

19. The method of making the2-((1H-indazol-5-yl)methylene)hydrazinecarbothioamide compound of claim 14, wherein the 2-((1H-indazol-5-yl)methylene)hydrazinecarbothioamide compound is obtained in an about 85% yield.

20. A method of making the 2-((1H-indazol-5-yl)methylene)hydrazinecarbothioamide compound of claim 1, the method comprising:
    condensing a thiosemicarbazide with a solution of indazole-5-carboxaldehyde using acetic acid as a catalyst; and
    obtaining the 2-((1H-indazol-5-yl)methylene)hydrazinecarbothioamide compound.

* * * * *